US009216151B2

(12) United States Patent
Kelliher et al.

(10) Patent No.: US 9,216,151 B2
(45) Date of Patent: *Dec. 22, 2015

(54) USE OF PUFAS FOR TREATING SKIN INFLAMMATION

(71) Applicant: Dignity Sciences Limited, Dublin (IE)

(72) Inventors: Adam Kelliher, London (GB); Angus Morrison, Isle of Lewis (GB); Phil Knowles, Cumbria (GB)

(73) Assignee: Dignity Sciences Limited. (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,375

(22) Filed: Jun. 26, 2014

(65) Prior Publication Data

US 2014/0309304 A1   Oct. 16, 2014

Related U.S. Application Data

(63) Continuation of application No. 14/203,837, filed on Mar. 11, 2014, which is a continuation of application No. 13/461,472, filed on May 1, 2012, now Pat. No. 8,729,126, which is a continuation of application No.

(Continued)

(30) Foreign Application Priority Data

Apr. 29, 2009 (GB) .................................. 0907413.9

(51) Int. Cl.
*A01N 37/00* (2006.01)
*A61K 31/20* (2006.01)
(Continued)

(52) U.S. Cl.
CPC ............. *A61K 9/0014* (2013.01); *A61K 31/202* (2013.01); *A61K 31/573* (2013.01); *A61K 45/06* (2013.01); *C07C 59/42* (2013.01)

(58) Field of Classification Search
CPC ........... A61K 8/36; A61K 8/37; A61K 31/20; A61K 31/201; A61K 31/202
USPC .......................................... 514/560; 554/224
See application file for complete search history.

(56) References Cited

U.S. PATENT DOCUMENTS 4,273,763 A    6/1981  Horrobin
4,309,415 A    1/1982  Horrobin
(Continued)

FOREIGN PATENT DOCUMENTS

EP   0139480   5/1952
EP   0035856   9/1981
(Continued)

OTHER PUBLICATIONS

Conrow et al., Org. Proc. Res. & Dev. 15:301-304 (2011).
(Continued)

*Primary Examiner* — Deborah D Carr
(74) *Attorney, Agent, or Firm* — Perkins Coie LLP

(57) ABSTRACT

The present invention provides a compound which is a polyunsaturated fatty acid (PUFA) derivative of formula (I),

I $$R_1O-C(=O)-CH_2-CH_2-Alk-CH_2-CH_2-CH_2-CH_3$$

or a pharmaceutically acceptable salt, or solvate thereof, for use in treating various skin disorders.

19 Claims, 5 Drawing Sheets

Related U.S. Application Data

13/318,290, filed as application No. PCT/GB2010/000844 on Apr. 29, 2010, now Pat. No. 8,536,223.

(60) Provisional application No. 61/177,811, filed on May 13, 2009.

(51) Int. Cl.
*A23D 9/00* (2006.01)
*A61K 9/00* (2006.01)
*A61K 31/202* (2006.01)
*A61K 31/573* (2006.01)
*A61K 45/06* (2006.01)
*C07C 59/42* (2006.01)

(56) References Cited

U.S. PATENT DOCUMENTS

| | | |
|---|---|---|
| 4,386,072 A | 5/1983 | Horrobin et al. |
| 4,388,324 A | 6/1983 | Horrobin |
| 4,444,755 A | 4/1984 | Horrobin |
| 4,826,877 A | 5/1989 | Stewart et al. |
| 4,888,326 A | 12/1989 | Horrobin |
| 4,898,885 A | 2/1990 | Horrobin |
| 4,965,075 A | 10/1990 | Horrobin et al. |
| 4,970,076 A | 11/1990 | Horrobin |
| 4,996,233 A | 2/1991 | Horrobin |
| 4,997,657 A | 3/1991 | Horrobin et al. |
| 5,145,686 A | 9/1992 | Horrobin et al. |
| 5,198,468 A | 3/1993 | Horrobin |
| 5,318,991 A | 6/1994 | Horrobin et al. |
| 5,324,748 A | 6/1994 | Horrobin |
| 5,328,691 A | 7/1994 | Horrobin et al. |
| 5,380,757 A | 1/1995 | Horrobin |
| 5,552,150 A | 9/1996 | Horrobin et al. |
| 5,562,913 A | 10/1996 | Horrobin |
| 5,580,556 A | 12/1996 | Horrobin |
| 5,583,159 A | 12/1996 | Horrobin et al. |
| 5,589,509 A | 12/1996 | Horrobin |
| 5,614,208 A | 3/1997 | Horrobin et al. |
| 5,618,558 A | 4/1997 | Horrobin et al. |
| 5,620,701 A | 4/1997 | Horrobin et al. |
| 5,663,202 A | 9/1997 | Horrobin et al. |
| 5,709,855 A | 1/1998 | Bockow et al. |
| 5,888,541 A | 3/1999 | Horrobin et al. |
| 6,069,168 A | 5/2000 | Horrobin et al. |
| 6,177,470 B1 | 1/2001 | Horrobin et al. |
| 6,479,544 B1 | 11/2002 | Horrobin |
| 6,630,157 B1 | 10/2003 | Horrobin et al. |
| 7,202,276 B2 | 4/2007 | Buchanan et al. |
| 7,888,393 B2 | 2/2011 | Bettle, III |
| 8,293,790 B2 | 10/2012 | Manku et al. |
| 8,536,223 B2 | 9/2013 | Kelliher et al. |
| 2003/0073930 A1 | 4/2003 | Morrissey et al. |
| 2003/0194446 A1 | 10/2003 | Akes et al. |
| 2007/0015438 A1 | 1/2007 | Lange et al. |
| 2008/0125487 A1 | 5/2008 | Das et al. |
| 2008/0161275 A1 | 7/2008 | Gjorstrup |
| 2008/0213357 A1 | 9/2008 | Hebard et al. |
| 2009/0176284 A1 | 7/2009 | Furihata et al. |
| 2010/0184727 A1 | 7/2010 | Roach et al. |
| 2010/0278948 A1 | 11/2010 | Courtin |
| 2010/0317735 A1 | 12/2010 | Hong et al. |
| 2011/0015415 A1 | 1/2011 | Singh et al. |
| 2011/0016585 A1 | 1/2011 | Pereira et al. |
| 2011/0039010 A1 | 2/2011 | Rein et al. |
| 2011/0059885 A1 | 3/2011 | Lea et al. |
| 2012/0142773 A1 | 6/2012 | Kelliher et al. |
| 2012/0213824 A1 | 8/2012 | Kelliher et al. |
| 2012/0232147 A1 | 9/2012 | Manku et al. |
| 2012/0264705 A1 | 10/2012 | Manku et al. |
| 2013/0101533 A1 | 4/2013 | Manku et al. |
| 2013/0102575 A1 | 4/2013 | Manku et al. |
| 2013/0267598 A1 | 10/2013 | Manku et al. |
| 2013/0274338 A1 | 10/2013 | Manku et al. |
| 2013/0331448 A1 | 12/2013 | Manku et al. |

FOREIGN PATENT DOCUMENTS

| | | | |
|---|---|---|---|
| EP | 0037175 | 10/1981 | |
| EP | 0078434 | 5/1983 | |
| EP | 0087863 | 9/1983 | |
| EP | 0087864 | 9/1983 | |
| EP | 0087865 | 9/1983 | |
| EP | 0115419 | 8/1984 | |
| EP | 0132089 | 1/1985 | |
| EP | 0173478 | 3/1986 | |
| EP | 0309086 | 3/1989 | |
| EP | 0409559 | 1/1991 | |
| EP | 0416855 | 3/1991 | |
| EP | 1852114 | 11/2007 | |
| EP | 2508180 | 10/2012 | |
| JP | 2006219454 | 8/2006 | |
| JP | 2006306812 | 11/2006 | |
| WO | WO9816215 | 4/1998 | |
| WO | WO9852556 | 11/1998 | |
| WO | WO2010020603 | 4/2000 | |
| WO | WO0103696 | 1/2001 | |
| WO | WO0201969 | 1/2002 | |
| WO | WO02089791 | 11/2002 | |
| WO | WO02092071 | 11/2002 | |
| WO | WO02096408 | 12/2002 | |
| WO | WO2007079224 | 7/2007 | |
| WO | WO2008070129 | 6/2008 | |
| WO | WO 2008070129 A2 * | 6/2008 | ........... A61K 31/202 |
| WO | WO2008114141 | 9/2008 | |
| WO | WO2010125330 | 11/2010 | |
| WO | WO2010125340 | 11/2010 | |
| WO | WO2013057284 | 4/2013 | |
| WO | WO2013057287 | 4/2013 | |
| WO | WO2013082265 | 6/2013 | |
| WO | WO2013112876 | 8/2013 | |
| WO | WO2013124479 | 8/2013 | |
| WO | WO2014022816 | 2/2014 | |

OTHER PUBLICATIONS

Desbois et al., "Antibacterial free fatty acids: activities, mechanisms of action and biotechnological potential," Appl. Microbiol. Biotechnol., (2010) 85:1629-1642.

Elshof et al. "Biocatalytic large-scale production of 12(S)-hydroperoxy-9(Z), 11⊊ octadecadienoic acid from hydrolysed safflower oil by a crude soybean-flour extract as lipoxygenase source," Rec. Trav. Chim Pays-Bas, 115, 11-12, p. 499-504 (1996).

Elshof et al., "Biocatalytic hydroxylation of linoleic acid in a double-fed batch system with lipoxygenase and cysteine," 100:6, pp. 246-251 (1999).

Erythema, Retrieved online [Feb. 11, 2014], Retrieved from URL:<http://umm.edu/health/medical/altmed/condition/erythema>.

Feldlaufer et al., "Antimicrobial activity of fatty acids aganst *Bacillus larvae*, the causative agent of American Foulbrood disease," Apidologie (1993) 24. pp. 95-99.

Huang et al., "Antimicrobial activity of n-6, n-7 and n-9 fatty acids and their esters for oral microorganisms," Archives of Oral Biology, 55 (2010), pp. 555-560.

Kawashima et al., "Subchronic (13-week) oral toxicity study of dihomo-γ-linolenic acid (DGLA) oil in rats," Food and Chemical Toxicology (2009).

Kiistala et al., "In vivo Separation of Epidermis by Production of Suction Blister," Lancet 1964:1444-1445 (1964).

Kiistala, "Suction blister device for separation fo viable epidermis from dermis," J. Invest. Dermatol. 50:129-137 (1968).

Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. Of Invest. Dermatol., vol. 96, No. 1, pp. 98-103 (1991).

(56) References Cited

OTHER PUBLICATIONS

Miller et al., "Guinea Pig Epidermins Generates Putative Anti-Inflammatory Metabolites from Fish Oil Polyunsaturated Acids," Lipids, vol. 24, No. 12 (1989).

Mosmann, J. Immunol. Meth. vol. 65, pp. 55-63 (1983).

Mundlein et al., "Comparison of Transepiderminal Water Losee (TEWL) Measurements with Two Novel Sensors Based on Different Sensing Principles," Sensors and Actuators A: Physical, 142(1):67-72 (2008).

Nijs et al., "Adult-onset asthma, is it really different?" Eur. Respir. Rev., vol. 22(127), pp. 44-52, Mar. 1, 2013.

PCT/EP12/070809 International Search Report dated Jan. 22, 2013.

PCT/EP12/070813 International Search Report dated Jan. 14, 2013.

PCT/EP2013/053677 International Search Report dated Jun. 19, 2013.

PCT/GB2010/000844 International Search Report dated Jul. 19, 2010.

PCT/US2012/67030 International Search Report dated Feb. 5, 2013.

PCT/US2013/023201 International Search Report dated Mar. 29, 2013.

PCT/US2013/053498 International Search Report dated Feb. 4, 2014.

Salgo et al., "Microdialysis documents changes in the micromilieu of psoriatic plaques under continuous systemic therapy," Experimental Dermatology 20:130-133 (2011).

Schreiner et al., "Transfer of Penicillin G and Ampicillin into Human Skin Blisters Induced by Suction," Scand. Journ. Infect. Dis. 14(Suppl.):233-237 (1978).

Tope, "Multi-electrode radio frequency resurfacing of ex vivo homan skin," Dermatol. Surg., 25:348-52 (1999).

Xue et al., "Optimization of Synthetic Conditions for the Preparation of Dihomogamma-Linolenic Acid from gamma-Linolenic Acid," Journ Amer. Oil Chemists' Soc., Jan. 2009, vol. 86, Issue 1, pp. 77-82.

Ziboh et al., "Dihomo-gamma-linolenic acid/15-hydroxyeicosatrienoic acid in skin inflammatory and proliferative processes," pp. 198-206 (2001).

Ziboh et al., Am. J. Clin. Nutr. 2000; 71(suppl):361S-6S.

* cited by examiner t=0 t=6hr t=0　　　　　　　　　　　　t=6hr t=0 t=6hr t=0　　　　　　　　　t=6hr

USE OF PUFAS FOR TREATING SKIN INFLAMMATION

CROSS REFERENCE TO RELATED APPLICATIONS

This application is a continuation of U.S. patent application Ser. No. 14/203,837 filed Mar. 11, 2014, entitled "USE OF PUFAS FOR TREATING SKIN INFLAMMATION," which is a continuation of U.S. patent application Ser. No. 13/461,472 filed May 1, 2012 (now U.S. Pat. No. 8,729,126), entitled "USE OF PUFAS FOR TREATING SKIN INFLAMMATION," which is a continuation of U.S. patent application Ser. No. 13/318,290 filed Feb. 24, 2012 (now U.S. Pat. No. 8,536,223), entitled "USE OF PUFAS FOR TREATING SKIN INFLAMMATION," which is a 35 USC §371 National Stage application of International Application No. PCT/GB2010/000844 filed Apr. 29, 2010, entitled "USE OF PUFAS FOR TREATING SKIN INFLAMMATION," which claims the benefit of priority to United Kingdom Patent Application No. GB 0907413.9 filed Apr. 29, 2009 and U.S. Provisional Application No. 61/177,811 filed May 13, 2009; the entirety of each of which is incorporated herein by reference.

FIELD OF THE INVENTION

The present invention relates to novel methods of treating skin inflammation, in particular skin inflammation caused by atopic eczema, contact dermatitis, psoriasis or uremic pruritis.

BACKGROUND OF THE INVENTION

Most common skin disorders and complaints comprise a number of different components. Thus, many skin disorders involve (a) hyperproliferation, (b) inflammation and/or (c) dehydration. Hyperproliferation involves a state of abnormally high cell division, which can lead to excess flaking skin. Inflammation involves swelling and redness of the skin, as well as sensations of increased heat, and pain in the skin. Dehydration involves loss of water from the skin and may be due, for example, to damage to the normally waterproof top layer of the skin (epidermis).

Inflammation of the skin (dermatitis) in mammals can result from a number of different etiologies. Dermatitis can be caused by eczema, in particular atopic eczema (atopic dermatitis), disseminated neurodermatitis, flexural eczema, infantile eczema, prurigo diathisique, contact dermatitis, (eg irritant contact dermatitis, allergic contact dermatitis and photocontact dermatitis), xerotic eczema, seborrheic eczema, dyshidrosis, discoid eczema, venous eczema, dermatitis herpetiformis, neurodermatitis and autoeczematisation. Dermatitis can also be caused by skin inflammation resulting from exposure to radiation, in particular exposure to ultraviolet radiation. Other causes of dermatitis includes uremic pruritis and autoimmune diseases, in particular lupus and psoriasis.

Inflammation of the skin causes rashes, redness, skin edema (swelling), itching, blistering, sensations of pain and/or heat and can be unsightly. The itchiness caused by inflammation can lead to scratching. Scratching of skin that is already damaged in some way can easily lead to the barrier of the epidermis being broken, resulting in bleeding, and secondary infection with pathogens. Such secondary infection can require treatment with antibiotics.

It is well known that when treating a skin condition that has a number of different components, i.e. hyperproliferative, inflammatory and/or dehydrative components, a number of different treatments may be used. Thus, in the treatment of psoriasis, for example, an antihyperproliferative may be used to treat the hyperproliferative component of the disease, an anti-inflammatory may be used to treat the inflammatory component and an emollient may be used to treat the dehydrative component.

The most common form of treatment for inflammation of the skin is oral and/or topical steroids. There are, however, drawbacks associated with steroid treatments. Common side effects associated with steroids include stunting of growth, thinning of the skin, muscle loss and osteoporosis.

The present invention relates to new methods for treating skin inflammation, in particular skin inflammation caused by atopic eczema, contact dermatitis, psoriasis or uremic pruritis, in mammals.

Eicosa-8Z, 11Z, 14Z-trienoic acid (Dihomo-γ-linolenic acid or DGLA) is a commercially available polyunsaturated fatty acid (PUFA). DGLA has the structure shown below.

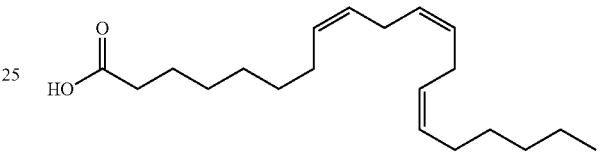

EP-A-0085579 describes the use of DGLA in combination with antipruritic lithium salts. EP-A-0173478 describes the use of DGLA in combination with anti-inflammatory glucocorticoids. In these applications, treatment with lithium salts and glucocorticoids is supplemented with DGLA, as both lithium salts and glucocorticoids are believed to block release of DGLA from endogenous structures in the body.

Advantageously, it has now been discovered that DLGA can be used effectively as a monotherapy.

5-Hydroxy-eicosa-6E,8Z,11Z-trienoic acid (5-HETrE)) is a commercially available PUFA derivative derived from mead acid. 5-HETrE has the structure shown below.

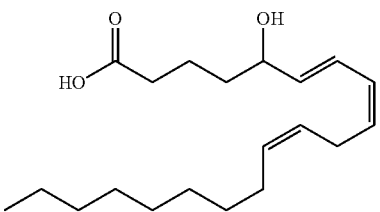 [SMILES: CCCCCCCC/C=C\C/C=C\C=C\C(O)CCCC(=O)O]

8-Hydroxy-eicosa-9E,11Z,14Z-trienoic acid (8-HETrE) is a commercially available PUFA derivative derived from eicosa-8Z,11Z,14Z-trienoic acid (Dihomo-γ-linolenic acid or DGLA). 8-HETrE has the structure shown below.

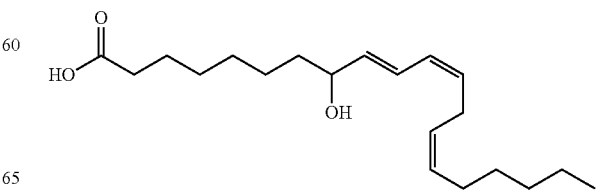

15-Hydroxy-eicosa-8Z,11Z,13E-trienoic acid (15-HETrE) is a commercially available PUFA derivative derived from eicosa-8Z,11Z,14Z-trienoic acid (Dihomo-γ-linolenic acid or DGLA). 15-HETrE has the structure shown below.

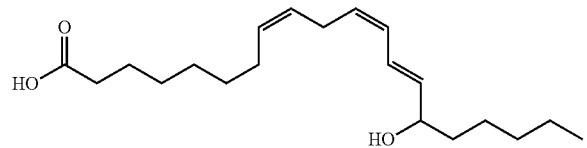 [SMILES: CCCCCC(O)/C=C/C=C\C/C=C\CCCCCCC(=O)O]

15-HETrE is known to have antiproliferative properties when applied directly to the skin (Xi, et al; Prostaglandins, Leukotrienes and Essential Fatty Acids (2000) 62(1), 13 to 19).

13-Hydroxy-octadeca-6Z,9Z,11E-γ-trienoic acid (13-HOTrE(γ)) is a commercially available PUFA derivative derived from gamma-linolenic acid (GLA). 13-HOTrE(γ) has the structure shown below.

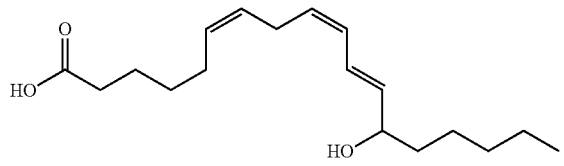 [SMILES: CCCCCC(O)/C=C/C=C\C/C=C\CCCCC(=O)O]

It has now been surprisingly found that DGLA, 5-HETrE, 8-HETrE, 15-HETrE, 13-HOTrE(γ) and their derivatives are clinically useful in treating skin inflammation, in particular skin inflammation caused by atopic eczema, contact dermatitis, psoriasis or uremic pruritis, by topical administration in mammals. A particular finding of the present invention is that these compounds reduce the level of COX-2 enzymes in the skin when applied topically. The COX-2 family of enzymes have been strongly linked to inflammation and have been found to be present in increased amounts in inflamed tissue.

SUMMARY OF THE INVENTION

The present invention therefore provides a compound which is a polyunsaturated fatty acid (PUFA) derivative of formula (I).

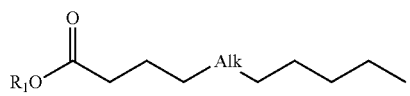

I or a pharmaceutically acceptable salt, or solvate thereof, wherein
-Alk- is —CH(OR$_2$)-[trans]CH=CH-[cis]CH=CH—CH$_2$-[cis]CH=CH—C$_3$H$_6$—, —(CH$_2$)$_3$—CH(OR$_2$)-[trans]CH=CH-[cis]CH=CH—CH$_2$-[cis]CH=CH—, —(CH$_2$)$_3$-[cis]CH=CH—CH$_2$-[cis]CH=CH-[trans]CH=CH—CH(OR$_2$)— or —CH$_2$-[cis]CH=CH—CH$_2$-[cis]CH=CH-[trans]CH=CH—CH(OR$_2$)—;
R$_1$ is a hydrogen atom; or
R$_1$ is a C$_1$-C$_6$ alkyl, C$_2$-C$_6$ alkenyl, C$_2$-C$_6$ alkynyl, C$_6$-C$_{10}$ aryl, 5- to 10-membered heteroaryl, C$_3$-C$_7$ carbocyclyl or 5- to 10-membered heterocyclyl group; or R$_1$ is a group of formula —CH$_2$—CH(OR$_3$)—CH$_2$—(OR$_4$), wherein R$_3$ and R$_4$ are each independently hydrogen atoms or —(C=O)—R$_6$, wherein R$_6$ is an aliphatic group having from 3 to 29 carbon atoms; or
R$_1$ is a group of formula —(CH$_2$OCH$_2$)$_m$OH, wherein m is an integer of from 1 to 200;
R$_2$ is a hydrogen atom; or
R$_2$ is a group —(C=O)—R$_5$, wherein R$_5$ is a C$_1$-C$_6$ alkyl, C$_2$-C$_6$ alkenyl, C$_2$-C$_6$ alkynyl, C$_6$-C$_{10}$ aryl, 5- to 10-membered heteroaryl, C$_3$-C$_7$ carbocyclyl or 5- to 100-membered heterocyclyl group, or R$_5$ is an aliphatic group having from 3 to 29 carbon atoms; or
R$_2$ is a group of formula —(CH$_2$OCH$_2$)$_n$OH, wherein n is an integer of from 1 to 200;
and wherein
said alkyl, alkenyl, alkynyl and aliphatic groups are the same or different and are each unsubstituted or substituted with 1, 2 or 3 unsubstituted substituents which are the same or different and are selected from halogen atoms and C$_1$-C$_4$ alkoxy, C$_2$-C$_4$ alkenyloxy, C$_1$-C$_4$ haloalkyl, C$_2$-C$_4$ haloalkenyl, C$_1$-C$_4$ haloalkoxy, C$_2$-C$_4$ haloalkenyloxy, hydroxyl, —SR', and —NR'R" groups where R' and R" are the same or different and represent hydrogen or unsubstituted C$_1$-C$_2$ alkyl;
said aryl, heteroaryl, carbocyclyl and heterocyclyl groups are the same or different and are each unsubstituted or substituted by 1, 2, 3 or 4 unsubstituted substituents which are the same or different and are selected from the halogen atoms, and cyano, nitro, C$_1$-C$_4$ alkyl, C$_1$-C$_4$ alkoxy, C$_2$-C$_4$ alkenyl, C$_2$-C$_4$ alkenyloxy, C$_1$-C$_4$ haloalkyl, C$_2$-C$_4$ haloalkenyl, C$_1$-C$_4$ haloalkoxy, C$_2$-C$_4$ haloalkenyloxy, hydroxyl, C$_1$-C$_4$ hydroxyalkyl, —SR' and —NR'R" groups wherein each R' and R" is the same or different and represents hydrogen or unsubstituted C$_1$-C$_4$ alkyl;
and wherein the PUFA derivative is in the form of a racemate, a stereoisomer or a mixture of stereoisomers,
which compound is for use in treating skin inflammation in a mammal, by topical administration.

DETAILED DESCRIPTION OF THE INVENTION

Figure 1:
FIG. 1 shows the results of an immunohistochemistry assay to determine the amount of COX-2 enzymes present in ex vivo porcine ear skin 0 and 6 hours after staining with diaminobenzidine.
Figure 1:
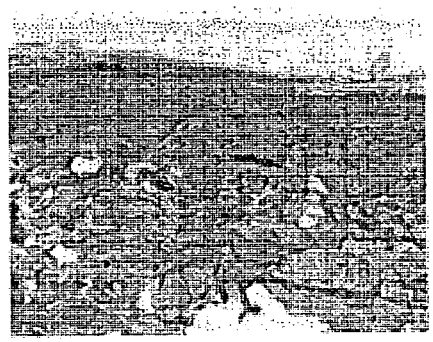

Preferably the alkyl, alkenyl, alkynyl and aliphatic groups are unsubstituted or substituted with 1, 2 or 3, preferably 1 or 2, more preferably 1, unsubstituted substituents which are the same or different and are selected from halogen atoms and $C_1$-$C_4$ alkoxy, hydroxyl, $C_1$-$C_4$ haloalkyl, $C_2$-$C_4$ haloalkenyl, $C_1$-$C_4$ haloalkoxy and —NR'R" wherein R' and R" are the same or different and represent hydrogen or $C_1$-$C_2$ alkyl. More preferred substituents are halogen, $C_1$-$C_4$ alkoxy, hydroxyl and —NR'R" groups where R' and R" are the same or different and represent hydrogen or unsubstituted $C_1$-$C_2$ alkyl. Particularly preferred substituents include hydroxyl and —NR'R" groups where R' and R" are the same and represent hydrogen.

When the alkyl, alkenyl, alkynyl and aliphatic groups above are substituted by two or three substituents, it is preferred that not more than two substituents are selected from hydroxyl. More preferably, not more than one substituent is selected from hydroxyl.

Most preferably, the alkyl, alkenyl and alkynyl groups have are unsubstituted.

As used herein, a $C_1$-$C_6$ alkyl group is a linear or branched alkyl group containing from 1 to 6 carbon atoms, for example a $C_1$-$C_4$ alkyl group containing from 1 to 4 carbon atoms, preferably a $C_1$-$C_2$ alkyl group containing from 1 to 2 carbon atoms. Examples of $C_1$-$C_4$ alkyl groups include methyl, ethyl, n-propyl, i-propyl, n-butyl, i-butyl and t-butyl. For the avoidance of doubt, where two alkyl groups are present in a compound of the present invention, the alkyl groups may be the same or different.

As used herein, a $C_2$-$C_6$ alkenyl group is a linear or branched alkenyl group having at least one double bond of either cis or trans configuration where applicable and containing from 2 to 6 carbon atoms, for example a $C_2$-$C_4$ alkenyl group containing from 2 to 4 carbon atoms, such as —CH=$CH_2$ or —$CH_2$—CH=$CH_2$, —$CH_2$—$CH_2$—CH=$CH_2$, —$CH_2$—CH=CH—$CH_3$, —CH=C($CH_3$)—$CH_3$ and —$CH_2$—C($CH_3$)=$CH_2$, preferably a $C_2$ alkenyl group having 2 carbon atoms. For the avoidance of doubt, where two alkenyl groups are present in a compound of the present invention, they may be the same or different.

As used herein, a $C_2$-$C_6$ alkynyl group is a linear or branched alkynyl group containing from 2 to 6 carbon atoms, for example a $C_2$-$C_4$ alkynyl group containing from 2 to 4 carbon atoms, preferably a $C_2$ alkynyl group containing 2 carbon atoms. Exemplary alkynyl groups include —C≡CH or —$CH_2$—C≡CH, as well as 1- and 2-butynyl, 2-methyl-2-propynyl, 2-pentynyl, 3-pentynyl, 4-pentynyl, 2-hexynyl, 3-hexynyl, 4-hexynyl and 5-hexynyl. For the avoidance of doubt, where two alkynyl groups are present in a compound of the present invention, they may be the same or different.

Preferably, said $C_1$-$C_6$ alkyl group is a $C_1$-$C_2$ alkyl group, said $C_2$-$C_6$ alkenyl group is a $C_2$ alkenyl group and said $C_2$-$C_6$ alkynyl group is a $C_2$ alkynyl group.

As used herein, a halogen atom is chlorine, fluorine, bromine or iodine.

As used herein, a $C_1$-$C_6$ alkoxy group or a $C_2$-$C_6$ alkenyloxy group is typically a said $C_1$-$C_6$ alkyl (e.g. a $C_1$-$C_4$ alkyl) group or a said $C_2$-$C_6$ alkenyl (e.g. a $C_2$-$C_4$ alkenyl) group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups, such as —$CX_3$ and —$OCX_3$ wherein X is a said halogen atom, for example chlorine and fluorine.

As used herein, a $C_1$-$C_4$ alkylthio or $C_2$-$C_4$ alkenylthio group is typically a said $C_1$-$C_4$ alkyl group or a $C_2$-$C_4$ alkenyl group respectively which is attached to a sulphur atom, for example —S—$CH_3$.

As used herein, a $C_1$-$C_4$ hydroxyalkyl group is a $C_1$-$C_4$ alkyl group substituted by one or more hydroxy groups. Typically, it is substituted by one, two or three hydroxy groups. Preferably, it is substituted by a single hydroxy group.

As used herein, a $C_6$-$C_{10}$ aryl group is a monocyclic or polycyclic, preferably monocyclic, aromatic ring containing form 6 to 10 carbon atoms, for example a $C_6$ aryl group containing 6 carbon atoms. Examples of such aryl groups include phenyl, naphthalene and azulene. Phenyl is preferred.

As used herein, a 5- to 10-membered heteroaryl group is a monocyclic or polycyclic, preferably monocyclic, 5- to 10-membered aromatic ring, such as a 5- or 6-membered ring, containing at least one heteroatom, for example 1, 2, 3 or 4 heteroatoms, selected from O, S and N. When the ring contains 4 heteroatoms these are preferably all nitrogen atoms. Examples include thienyl, furyl, pyrrolyl, imidazolyl, thiazolyl, isothiazolyl, pyrazolyl, oxazolyl, isoxazolyl, trizolyl, thiadiazolyl, oxadiazolyl, pyridinyl, pyridazinyl, pyrimidinyl, pyrazinyl, triazinyl and tetrazolyl groups. Thienyl, pyrrolyl, imidazolyl, thiazolyl, isothiazolyl, pyrazolyl, oxazolyl, isoxazolyl, trizolyl, pyridinyl, pyridazinyl, pyrimidinyl and pyrazinyl groups are preferred, e.g. pyrrolyl, imidazolyl, thiazolyl, isothiazolyl, pyrazolyl, oxazolyl, isoxazolyl, trizolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, e.g. pyridinyl, pyridazinyl, pyrimidinyl, pyrazinyl, pyrrolyl and triazinyl, most preferably pyridinyl.

As used herein, a 5- to 10-membered heterocyclyl group is a non-aromatic, saturated or unsaturated monocyclic or polycyclic, preferably monocyclic, $C_{5-10}$ carbocyclic ring in which one or more, for example 1, 2, 3, or 4, of the carbon atoms are replaced with a moiety selected from N, O, S, S(O) and $(SO)_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. Typically, the 5- to 10-membered heterocyclyl ring is a 5- to 6-membered ring.

Suitable heterocyclyl groups include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxo-thiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadizol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidzolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties.

For the avoidance of doubt, although the above definitions of heteroaryl and heterocyclyl groups refer to an "N" moiety which can be present in the ring, as will be evident to a skilled chemist the N atom will be protonated (or will carry a substituent as defined below) if it is attached to each of the adjacent ring atoms via a single bond.

As used herein, a $C_3$-$C_7$ carbocyclic group is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants, more particularly cyclopentyl and cyclohexyl. A $C_3$-$C_7$ carbocyclyl group also includes $C_3$-$C_7$ carbocyclyl groups described above but wherein one or more ring carbon atoms are replaced by a group —C(O)—. More preferably 0, 1 or 2 ring carbon atoms (most preferably 0) are replaced by —C(O)—. Most preferably, said $C_3$-$C_7$ carbocyclyl group is cyclohexyl.

Typically the aryl, heteroaryl, heterocyclyl and carbocyclyl groups in $R_1$ and $R_5$ are unsubstituted or substituted by 1, 2, 3, or 4 unsubstituted substituents, for example by 1, 2 or 3 unsubstituted substituents. Preferred substituents include halogen atoms and $C_1$-$C_4$ alkyl, $C_2$-$C_4$ alkenyl, $C_1$-$C_4$ alkoxy, $C_2$-$C_4$ alkenyloxy, $C_1$-$C_4$ haloalkyl, $C_2$-$C_4$ haloalkenyl, $C_1$-$C_4$ haloalkoxy, $C_2$-$C_4$ haloalkenyloxy, hydroxyl, mercapto, cyano, nitro, $C_1$-$C_4$ hydroxyalkyl, $C_2$-$C_4$ hydroxyalkenyl, $C_1$-$C_4$ alkylthio, $C_2$-$C_4$ alkenylthio and —N'R" groups wherein each R' and R" is the same or different and represents hydrogen or $C_1$-$C_4$ alkyl. More preferred substituents include halogen atoms and unsubstituted $C_1$-$C_4$ alkyl, $C_1$-$C_4$ alkoxy, hydroxyl, $C_1$-$C_4$ haloalkyl, $C_1$-$C_4$ haloalkoxy, $C_1$-$C_4$ hydroxyalkyl, cyano, nitro, —SR' and —NR'R" groups where R' and R" are the same or different and represent hydrogen or unsubstituted $C_1$-$C_2$ alkyl. More preferred substituents include halogen atoms, hydroxyl groups and $C_1$-$C_2$ alkyl and $C_1$-$C_2$ alkoxy groups.

Most preferably, the aryl, heteroaryl, heterocyclyl and carbocyclyl groups above are unsubstituted.

When the aryl, heteroaryl, heterocyclyl and carbocyclyl groups in $R_1$ and $R_5$ are substituted by two, three or four substituents, it is preferred that not more than two substituents are selected from hydroxyl, cyano and nitro. More preferably, not more than one substituent is selected from hydroxyl, cyano and nitro.

As used herein, a pharmaceutically salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g.; calcium or magnesium) hydroxides and organic bases such as alkyl amines, aralkyl amines and heterocyclic amines.

The term "solvate" refers to a complex or aggregate formed by one or more molecules of a solute, i.e. compounds of the invention or pharmaceutically-acceptable salts thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The compounds of the invention may contain a chiral center. Accordingly, they can be used in the form of a racemic mixture, an enantiomer, or a mixture enriched in one or more stereoisomer. The scope of the invention as described and claimed encompasses the racemic forms of the compounds of the invention as well as the individual enantiomers, and stereoisomer-enriched mixtures.

It will be appreciated that the term "or a pharmaceutically acceptable salt or solvate thereof" is intended to include all permutations of salts and solvates, such as solvates of pharmaceutically-acceptable salts of compounds of the invention.

$R_5$ and $R_6$ may be an aliphatic group having 3 to 29 carbon atoms. Typically, the aliphatic group is not cyclic. The aliphatic group is typically linear or branched, preferably linear. Typically, the aliphatic group has 7 to 25 carbon atoms, more preferably 11 to 25 carbon atoms. The aliphatic group is typically unsubstituted or substituted with one hydroxyl group. The aliphatic group is preferably unsubstituted.

Aliphatic groups may be saturated, monounsaturated or polyunsaturated. Saturated aliphatic groups are preferred.

Typically, saturated aliphatic groups have from 7 to 25 carbon atoms, preferably 11 to 17 carbon atoms.

Monounsaturated aliphatic groups typically contain a single C=C double bond. The double bond has cis or trans configuration. The single double bond may be present at any point in the aliphatic group, it is typically 7 or 9 carbon atoms from the end of the aliphatic group distal to the (C=O) group to which the aliphatic group is attached. Typically, monounsaturated aliphatic groups have from 7 to 25 carbon atoms, preferably 15 to 23 carbon atoms.

Polyunsaturated aliphatic groups typically contain two or more C=C double bonds, for example 2, 3, 4, 5 or 6 C=C double bonds. Each double bond may have cis or trans configuration. The double bonds may be present at any point in the aliphatic chain, but typically, the C=C double bond furthest from the (C=O) group to which the aliphatic group is attached is 3, 6 or 9 carbon atoms from the end of the aliphatic group distal to the (C=O) group to which the aliphatic group is attached. Typically, polyunsaturated aliphatic groups have from 7 to 25 carbon atoms, preferably 15 to 23 carbon atoms.

Typically, said aliphatic group is the group R, wherein R—$CO_2H$ is a fatty acid. Preferably, said fatty acid is lauric acid, myristic acid, palmitic acid, stearic acid palmitoleic acid, cis-vaccenic acid, oleic acid, eicosenoic acid, erucic acid, nervonic acid, alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, linoleic acid, gamma-linolenic acid, eicosadienoic acid, dihommo-gamma-linolenic acid, arachidonic acid, docosadienoic acid, adrenic acid, docosapentaenoic acid, or mead acid. More preferably, said fatty acid is lauric acid, myristic acid, palmitic acid, or stearic acid.

In one embodiment, the aliphatic group having 3 to 29 carbon atoms is the aliphatic group of a PUFA derivative of formula (I) as defined herein, i.e. the aliphatic group is of formula —$(CH_3)_3$-Alk-$(CH_2)_4CH_3$, where -Alk- is as defined herein.

In a preferred embodiment, the aliphatic group having 3 to 29 carbon atoms is the aliphatic group of dihommo-gamma-linolenic acid or 15-hydroxyeicosatrienoic acid, i.e. the aliphatic group is —$(CH_2)_6$—CH=CH—$CH_2$—CH=CH—$CH_2$—CH=CH—$(CH_2)_4CH_3$, wherein all of the C=C double bonds have cis configuration, or —$(CH_2)_6$-[cis]CH=CH—$CH_2$-[cis]CH=CH-[trans]CH=CH—CH(OH)—$(CH_2)_4CH_3$. Preferably, the aliphatic group having 3 to 29 carbon atoms is the aliphatic group of 15-hydroxyeicosatrienoic acid, i.e. the aliphatic group is —$(CH_2)_6$-[cis]CH=CH—$CH_2$-[cis]CH=CH-[trans]CH=CH—CH(OH)—$(CH_2)_4CH_3$.

In a more preferred embodiment, the PUFA derivative of formula (I) is of formula R'(C=O)O—CH₂—CH(O(C=O)R')—CH₂—O(C=O)R', wherein each R' is the aliphatic group of 15-hydroxeicosatrienoic acid, i.e. R' is —(CH₂)₆-[cis]CH=CH—CH₂-[cis]CH=CH-[trans]CH=CH—CH(OH)—(CH₂)₄CH₃. Thus, the PUFA derivative of formula (I) is preferably R₃ is typically —(C=O)—R₆, wherein R₆ is as defined herein.

R₄ is typically —(C=O)—R₆, wherein R₆ is as defined herein.

Preferably, both R₃ and R₄ are —(C=O)—R₆, wherein each R₆ may be the same or different and is as defined herein.

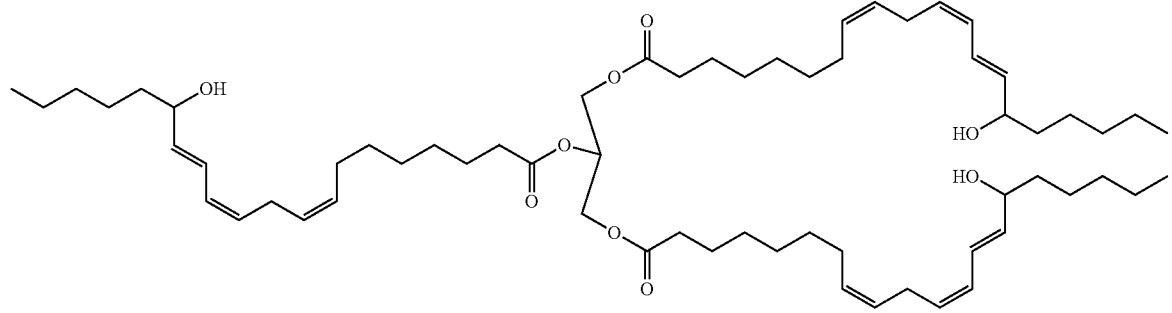 [SMILES: CCCCCC(O)/C=C/C=C\C/C=C\CCCCCCC(=O)OCC(COC(=O)CCCCCC/C=C\C/C=C\C=C\C(O)CCCCC)OC(=O)CCCCCC/C=C\C/C=C\C=C\C(O)CCCCC]

It is to be understood that the left hand side of the -Alk- moiety is bonded to the unsaturated carbon chain bearing the —COOR₁ moiety and the right hand side of the -Alk- group is bonded to the saturated carbon chain.

Typically, -Alk- is —CH(OR₂)-[trans]CH=CH-[cis]CH=CH—CH₂-[cis]CH=CH—C₃H₆—, —(CH₂)₃—CH(OR₂)-[trans]CH=CH-[cis]CH=CH—CH₂-[cis]CH=CH—, or —(CH₂)₃-[cis]CH=CH—CH₂-[cis]CH=CH-[trans]CH=CH—CH(OR₃)—. Preferably, -Alk- is —CH₂)₃-[cis]CH=CH—CH₂-[cis]CH=CH—CH₂-[cis]CH=CH—.

Typically, R₁ is a hydrogen atom; or R₁ is a C₁-C₄ alkyl, C₂-C₄ alkenyl, C₂-C₄ alkynyl, C₅ aryl, 5- to 6-membered heteroaryl, C₃-C₆ carbocyclyl or 5- to 6-membered heterocyclyl group; or R₁ is a group of formula —CH₂—CH(OR₃)—CH₂—(OR₄), wherein R₃ and R₄ are as defined herein; or R₁ is a group of formula —(CH₂OCH₂)ₘOH, wherein m is as defined herein, wherein said alkyl, alkenyl and alkynyl groups are the same or different and are each unsubstituted or substituted with 1, or 2 unsubstituted substituents which are the same or different and are selected from halogen atoms, C₁-C₄ alkoxy, hydroxyl, and —NR'R" groups where R' and R" are the same or different and represent hydrogen or unsubstituted C₁-C₂ alkyl; and said aryl, heteroaryl, carbocyclyl and heterocyclyl groups are the same or different and are each unsubstituted or substituted by 1, 2 or 3 unsubstituted substituents which are the same or different and are selected from halogen atoms, and cyano, nitro, C₁-C₄ alkyl, C₁-C₄ alkoxy, and —NR'R" groups wherein each R' and R" is the same or different and represents hydrogen or unsubstituted C₁-C₂ alkyl group.

Preferably, R₁ is a hydrogen atom; or R₁ is an unsubstituted C₁-C₄ alkyl group; or R₁ is a group of formula —CH₂—CH(OR)₃)—CH₂—(OR₄), where R₃ and R₄ are as defined herein; or R₁ is a group of formula —(CH₂OCH₂)ₘOH, wherein m is as defined herein.

More preferably, R₁ is a hydrogen atom; or R₁ is a group of formula —CH₂—CH(OR₃)—CH₂—(OR₄), wherein R₃ and R₄ are as defined herein, and wherein at least one R₃ or R₄ is —(C=O)—R₆, wherein R₆ is as defined herein.

Most preferably, R₁ is a hydrogen atom.

m is typically an integer of from 5 to 150, preferably from 10 to 50.

Typically, when R₃ and R₄ are both —(C=O)—R₆, then R₅ is not an aliphatic group having 3 to 29 carbon atoms.

R₆ is an aliphatic group having from 3 to 29 carbon atoms, as defined herein. Typically, said aliphatic group is saturated. Typically, R₆ is an aliphatic group having 7 to 25 carbon atoms, preferably 11 to 17 carbon atoms. Preferably, R₆ is a group R, wherein R—CO₂H is auric acid, myristic acid, palmitic acid, or stearic acid.

Typically, R₂ is a hydrogen atom; or R₂ is a group —(C=O)—R₅, wherein R₅ is a C₁-C₄ alkyl, C₂-C₄ alkenyl, C₂-C₄ alkynyl, C₆ aryl, 5- to 6-membered heteroaryl, C₃-C₆ carbocyclyl or 5 to 6-membered heterocyclyl group, or R₅ is an aliphatic group having from 3 to 29 carbon atoms; or R₂ is a group of formula —(H₂OCH₂)ₙOH, wherein n is as defined herein, wherein said alkyl, alkenyl and alkynyl groups are the same or different and are each unsubstituted or substituted with 1, or 2 unsubstituted substituents which are the same or different and are selected from halogen atoms, C₁-C₄ alkoxy, hydroxyl, and —NR'R" groups where R' and R" are the same or different and represent hydrogen or unsubstituted C₁-C₂ alkyl; and said aryl, heteroaryl, carbocyclyl and heterocyclyl groups are the same or different and are each unsubstituted or substituted by 1, 2 or 3 unsubstituted substituents which are the same or different and are selected from halogen atoms, and cyano, nitro, C₁-C₄ alkyl, C₁-C₄ alkoxy, and —NR'R" groups wherein each R' and R" is the same or different and represents hydrogen or unsubstituted C₁-C₂ alkyl group.

Preferably, R₂ is a hydrogen atom; or R₂ is a group —(C=O)—R₅, wherein R₅ is unsubstituted C₁-C₄ alkyl; or R₂ is a group —(C=O)—R₅, wherein R₅ is an aliphatic group having from 3 to 29 carbon atoms; or R₂ is a group of formula —(CH₂OCH₂)ₙOH, wherein n is as defined herein.

More preferably, R₂ is a hydrogen atom; or R₂ is a group —(C=O)—R₅, wherein R₅ is an aliphatic group having from 3 to 29 carbon atoms; or R₂ is a group of formula —(CH₂OCH₂)ₙOH, wherein n is as defined herein.

Most preferably, R₂ is a hydrogen atom.

n is typically an integer of from 5 to 150, preferably from 10 to 50.

When R₅ is an aliphatic group having 3 to 29 carbon atoms, said aliphatic group is as defined herein. Typically, said aliphatic group is saturated. Typically, R₅ is an aliphatic group having 7 to 25 carbon atoms, preferably 11 to 17 carbon atoms. Preferably, $R_5$ is a group R, wherein R—$CO_2H$ is auric acid, myristic acid, palmitic acid, or stearic acid.

In one embodiment, the PUFA derivative of formula (I) is present as a racemic mixture of the R and S enantiomers.

In another embodiment, the PUFA derivative of formula (I) is present as the R enantiomer.

In another embodiment, the PUFA derivative of formula (I) is present as the S enantiomer.

Typically, the mammal is a human.

In a preferred embodiment, -Alk- is —CH($OR_2$)-[trans]CH=CH-[cis]CH=CH—$CH_2$-[cis]CH=CH—$C_3H_6$—, —($CH_2$)$_3$—CH($OR_3$)-[trans]CH=CH-[cis]CH=CH—$CH_2$-[cis]CH=CH—, or —($CH_2$)$_3$-[cis]CH=CH—$CH_2$-[cis]CH=CH-[trans]CH=CH—CH($OR_2$)—; $R_1$ is a hydrogen atom, an unsubstituted $C_1$-$C_4$ alkyl group, or a group of formula —$CH_2$—CH($OR_3$)—$CH_2$—($OR_4$), wherein $R_3$ and $R_4$ are each independently hydrogen atoms or —(C=O)—$R_6$, wherein $R_6$ is a linear aliphatic group having from 11 to 25 carbon atoms, which aliphatic group is unsubstituted or substituted with one hydroxyl group, or $R_1$ is a group of formula —($CH_2OCH_2$)$_m$OH, wherein m is an integer of from 5 to 150; and $R_2$ is a hydrogen atom, a group of —(C=O)—$R_5$, wherein $R_5$ is unsubstituted $C_1$-$C_4$ alkyl, or a group —(C=O)—$R_5$, wherein $R_5$ is a linear aliphatic group having from 11 to 25 carbon atoms, which aliphatic group is unsubstituted or substituted with one hydroxyl group; or $R_2$ is a group of formula —($CH_2OCH_2$)$_n$OH, wherein n is an integer of from 5 to 150.

In a more preferred embodiment, -Alk- is —($CH_2$)$_3$-[cis]CH=CH—$CH_2$-[cis]CH=CH-[trans]CH=CH—CH($OR_2$)—; $R_1$ is a hydrogen atom, an unsubstituted $C_1$-$C_4$ alkyl group, or a group of formula —$CH_2$—CH($OR_3$)—$CH_2$—($OR_4$), wherein $R_3$ and $R_4$ are each independently hydrogen atoms or —(C=O)—$R_6$, wherein $R_6$ is a linear aliphatic group having from 11 to 25 carbon atoms, which aliphatic group is unsubstituted or substituted with one hydroxyl group, or $R_1$ is a group of formula —($CH_2OCH_2$)$_m$OH, wherein m is an integer of from 5 to 150; and $R_2$ is a hydrogen atom, a group —(C=O)—$R_5$, wherein $R_5$ is unsubstituted $C_1$-$C_4$ alkyl, or a group —(C=O)—$R_5$, wherein $R_5$ is a linear aliphatic group having from 11 to 25 carbon atoms, which aliphatic group is unsubstituted or substituted with one hydroxyl group; or $R_2$ is a group of formula —($CH_2OCH_2$)$_n$OH, wherein n is an integer of from 5 to 150.

In a most preferred embodiment, -Alk- is —($CH_2$)$_3$-[cis]CH=CH—$CH_2$-[cis]CH=CH-[trans]CH=CH—CH($OR_2$)—; $R_1$ is a hydrogen atom, a group of formula —$CH_2$—CH($OR_3$)—$CH_2$—($OR_4$), wherein $R_3$ and $R_4$ are each independently hydrogen atoms or —(C=O)—$R_6$, wherein $R_6$ is an unsubstituted linear, saturated aliphatic group having from 11 to 17 carbon atoms, and wherein at least one of $R_3$ or $R_4$ is —(C=O)—$R_6$; and $R_2$ is a hydrogen atom, or a group —(C=O)—$R_5$, wherein $R_5$ is an unsubstituted linear, saturated aliphatic group having from 11 to 17 carbon atoms, or $R_2$ is a group of formula —($CH_2OCH_2$)$_n$OH, wherein n is an integer of from 10 to 50.

Typically, in the compounds of the present invention, including the preferred embodiments set out above, (a) $R_1$ is a group of formula —$CH_2$—CH($OR_3$)—$CH_2$—($OR_4$), wherein $R_3$ and $R_4$ each independently represent a hydrogen atom or —(C=O)—$R_6$, wherein $R_6$ is a saturated aliphatic group having from 3 to 29 carbon atoms, wherein at least one of $R_3$ or $R_4$ is —(C=O)—$R_6$; or (b) $R_1$ is a group of formula —($CH_2OCH_2$)$_m$OH, wherein m is as defined herein; and/or (c) $R_2$ is a group —(C=O)—$R_5$, wherein $R_5$ is a saturated aliphatic group having from 3 to 29 carbon atoms; or (d) $R_2$ is a group of formula —($CH_2OCH_2$)$_n$OH, wherein n is as defined herein. Such compounds will be particularly lipophilic, which is advantageous in some instances.

In this preferred embodiment, preferably (a) $R_1$ is a group of formula —$CH_2$—CH($OR_3$)—$CH_2$—($OR_4$), wherein $R_3$ and $R_4$ are each independently hydrogen atoms or —(C=O)—$R_6$, one of $R_3$ or $R_4$ is —(C=O)—$R_6$; and/or (c) $R_2$ is a group —(C=O)—$R_5$, wherein $R_5$ is a saturated aliphatic group having 3 to 29 carbon atoms.

In a more preferred embodiment, both $R_1$ and $R_2$ are hydrogen atoms.

In a particularly preferred embodiment, -Alk- is —($CH_2$)$_3$-[cis]CH=CH—$CH_2$-[cis]CH=CH-[trans]CH=CH—CH($OR_2$)—, and $R_1$ and $R_2$ are both hydrogen atoms. In this embodiment, the PUFA derivative of formula (I) is 15-HETrE and is represented by the formula

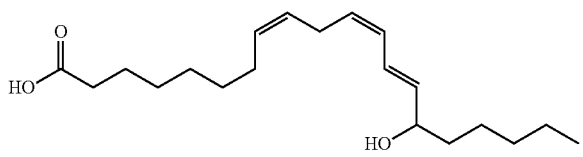 [SMILES: CCCCCC(O)/C=C/C=C\C/C=C\CCCCCCC(=O)O]

Typically, compounds of the invention are administered as one or more treatments per day, preferably from 1 to 4 treatments per day, more preferably from 1 to 2 treatments per day.

Typically, compounds of the invention are administered at a daily dosage of from 0.1 mg/m²/day to 1 kg/m²/day, preferably from 1 mg/m²/day to 100 g/m²/day, more preferably from 10 mg/m²/day to 10 g/m²/day, most preferably from 100 mg/m²/day to 1 g/m²/day.

Skin inflammation includes rashes, hives, blisters and/or wheals and may be caused by eczema, exposure to radiation, autoimmune diseases, and/or uremic pruritis.

In a preferred embodiment, the skin inflammation is caused by atopic eczema, contact dermatitis, psoriasis or uremic pruritis.

In a further preferred embodiment, the skin inflammation is caused by exposure of the skin to electromagnetic radiation. This includes, for example, exposure to sunlight, heat, X-rays or radioactive materials. Thus, in this embodiment, the compound of the present invention is typically used to treat sunburn.

The term eczema is applied to a wide range of skin conditions with a variety of aetiologies. In general, eczema is categorised by inflammation of the epidermis. Common symptoms associated with eczema include dryness, recurring skin rashes, redness, skin edema (swelling), itching, dryness, crusting, flaking, blistering, cracking, oozing, and bleeding. Eczema includes atopic eczema (atopic dermatitis), contact dermatitis, xerotic eczema, seborrhoeic dermatitis, dyshydrosis, discoid eczema, venous eczema, dermatitis herpetiformus, neurodermatitis, and autoeczematisation. Eczema is typically atopic eczema or contact dermatitis.

Atopic eczema is primarily aggravated by contact with or intake of allergens, which include animal hair and dander, food allergens, for example nuts or shellfish, or drugs, for example penicillin.

Contact dermatitis includes allergic contact dermatitis, irritant contact dermatitis and photocontact dermatitis.

Electromagnetic radiation includes radio waves, microwaves, terahertz radiation, infrared radiation, visible light, ultraviolet radiation, X-rays and gamma rays. Electromagnetic radiation is preferably infrared radiation, visible light, ultraviolet radiation, X-rays and gamma rays, more preferably ultraviolet radiation, X-rays and gamma rays.

Autoimmune diseases can involve an autoimmune response against the skin. Examples of such autoimmune diseases are lupus and psoriasis.

Uremic pruritis is a disorder of the skin associated with chronic renal failure. It also frequently affects patients undergoing dialysis treatment.

Typically, the compound of the present invention is co-administered with a corticosteroid.

Suitable corticosteroids to be used for co-administration with compounds of the invention are clobetasol diproprionate, betamethasone diproprionate, halbetasol proprionate, diflorasone diacetate, fluocinonide, halcinoide, amcinonide, desoximetasone, trimcinolone acetonide, mometasone furoate, fluticasone propionate, fluocinolone acetonide, hydrocortisone valerate, hydrocortisone butyrate, triaminalone acetonide, desonide, prednicarbate, prednisolone, methylprednisolone, dexmethasone, naflocort, deflazacort, halopredone acetate, budesonide, beclomethasone dipropionate, hydrocortisone, clocortolone pivalate, methylprednisolone aceponate, dexamethasone palmitoate, tipredane, hydrocortisone aceponate, alclometasone dipropionate, halometasone, methylprednisolone suleptanate, rimexolone, prednisolone farnesylate, ciclesonide, deprodone propionateloteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Preferred corticosteroids corticosteriods to be used for co-administration with compounds of the invention are clobetasol diproprionate, betamethasone diproprionate, halbetasol proprionate, diflorasone diacetate, fluocinonide, halcinonide, amcinonide, desoximetasone, triamcinolone acetonide, mometasone furoate, fluticasone propionate, fluocinolone acetonide, hydrocortisone valerate, hydrocortisone butyrate, triamcinalone acetonide, desonide, and prednicarbate.

Any reference to corticosteroids within the scope of the present invention includes a reference to salts or derivatives thereof which may be formed from the corticosteroids. Examples of possible salts or derivatives include: sodium salts, sulphobenzoates, phosphates, isonicotinates, acetates, propionates, dihydrogen phosphates, palmitates, pivaiates, farnesylates, aceponates, suleptanates, prednicarbates, furoates or acetonides. In some cases the corticosteroids may also occur in the form of their hydrates.

It is a particular finding of the present invention that co-administration of a compound of the present invention with a corticosteroid enables the amount of corticosteroid administered to be reduced, without reducing the efficacy of the treatment. Thus, in a preferred embodiment, the compound of the present invention is co-administered with a corticosteroid, wherein the corticosteroid is administered at a daily dosage of 50% or less, preferably 25% or less, more preferably 10% or less, most preferably 5% or less, of the recommended daily dosage of said corticosteroid in said mammal.

The person skilled in the art is well aware of the recommended daily dosages of corticosteroids in mammals. For example, the recommended daily dosage of hydrocortisone in humans is approximately 0.35 g/m²/day. The recommended daily dosage of clobetasol propionate in humans is 0.009 to 0.018 g/m²/day.

Thus, compounds of the present invention are typically coadministered with hydrocortisone, wherein the daily dosage of hydroxortisone is 0.175 g/m²/day or less, preferably 0.0875 g/m²/day or less, more preferably 0.035 g/m²/day, most preferably 0.0175 g/m²/day or less. Compounds of the present invention are typically coadministered with clobetasol propionate, wherein the daily dosage of clobetasol propionate is 0.009 g/m²/day or less, preferably 0.0045 g/m²/day or less, more preferably 0.0018 g/m²/day or less, most preferably 0.0009 g/m²/day or less.

The compounds of the present invention are typically coadministered with a further therapeutic agent, which is not a corticosteroid, which is effective in treating skin conditions/diseases. Such therapeutic agents are well known to the skilled person and include, but are not limited to, immunomodulators, antiobiotics, immunosuppressants and anti-itch drugs.

Compounds of the invention are typically commercially available, or may be prepared by analogy with known methods. Thus, for example, both DGLA and 15-HETrE are commercially available. These available fatty acids can easily be derivatised to obtain PUFA derivatives of formula (I) by known methods.

For example, PUFA derivatives of formula (I) as defined herein, wherein $R_1$ is a $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ carbocyclyl or 5- to 10-membered heterocyclyl group; or $R_1$ is a group of formula —$CH_2$—$CH(OR_3)$—$CH_2$—$(OR_4)$, wherein $R_3$ and $R_4$ are as defined herein; or $R_1$ is a group of formula —$(CH_2OCH_2)_m$OH, wherein m is as defined herein, can be prepared by esterifying a compound of formula

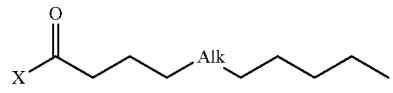

wherein -Alk- is as defined herein and X is a leaving group, for example a halogen atom, a tosylate or mesylate group with an alcohol of formula $R_1'$—OH, wherein $R_1'$ is a $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_7$ carbocyclyl or 5- to 10-membered heterocyclyl group; or $R_1'$ is a group of formula —$CH_2$—$CH(OR_3)$—$CH_2$—$(OR_4)$, wherein $R_3$ and $R_4$ are as defined herein; or $R_1'$ is a group of formula —$(CH_2OCH_2)_m$OH, wherein m is as defined herein, to obtain a PUFA derivative of formula (I) as defined herein. Alternatively, X may be a hydroxyl group. In that case, the reaction is preferably carried out under acidic conditions, or in the presence of a suitable catalyst, for example pyridine. Compounds of formula $R_1'$—OH are typically commercially available or may be prepared by analogy with known methods.

When -Alk- is —CH(OR₂)-[trans]CH═CH-[cis]CH═CH—CH₂-[cis]CH═CH—C₃H₆—, —(CH₂)₃)—CH(OR₂)-[trans]CH═CH-[cis]CH═CH—CH₂-[cis]CH═CH—, or —(CH₂)₃-[cis]CH═CH—CH₂-[cis]CH═CH-[trans]CH═CH—CH(OR₂)—, PUFA derivatives of formula (I) as defined herein, wherein $R_2$ is a group of —(C═O)—$R_5$, wherein $R_5$ is a $C_1$-$C_6$ alkyl, $C_2$-$C_6$ alkenyl, $C_2$-$C_6$ alkynyl, a $C_6$-$C_{10}$ aryl, a 5- to 10-membered heteroaryl, a $C_3$-$C_7$ carbocyclyl or a 5- to 10-membered heterocyclyl group, or $R_5$ is an aliphatic group having from 3 to 29 carbon atoms, can be prepared by treating a compound of formula (I) as defined herein, wherein -Alk- is —CH(OR₂)-[trans]CH═CH-[cis]CH═CH—CH₂-[cis]CH═CH—CH₃H₆—, —(CH₂)₃—CH(OR₂)-[trans]CH═CH-[cis]CH═CH—CH₂-[cis]CH═CH—, or —(CH₂)₃-[cis]CH═CH—CH₂-[cis]CH═CH-[trans]CH═CH—CH(OR₂)—, and $R_2$ is a hydrogen atom, with a carboxylic acid derivative Y—(C=O)—R'$_5$, wherein R'$_5$ is a C$_1$-C$_6$ alkyl, C$_2$-C$_6$ alkenyl, C$_2$-C$_6$ alkynyl, a C$_6$-C$_{10}$ aryl, a 5- to 10-membered heteroaryl, a C$_3$-C$_7$ carbocyclyl or a 5- to 10-membered heterocyclyl group, or R'$_5$ is an aliphatic group having from 3 to 29 carbon atoms, and Y is a leaving group, for example a halogen atom, a tosylate or mesylate group. Compounds of formula Y—(C=O)—R'$_5$ are typically commercially available or may be prepared by analogy with known methods.

When -Alk- is —CH(OR$_2$)-[trans]CH=CH-[cis]CH=CH—CH$_2$-[cis]CH=CH—C$_3$H$_6$—, —(CH$_2$)$_3$—CH(OR$_2$)-[trans]CH=CH-[cis]CH=CH—CH$_2$-[cis]CH=CH—, or —(CH$_2$)$_3$-[cis]CH=CH—CH$_2$-[cis]CH=CH-[trans]CH=CH—CH(OR$_2$)—, PUFA derivatives of formula (I) as defined herein, wherein R$_2$ is a group of formula —(CH$_2$OCH$_2$)$_n$OH, wherein n is as defined herein, can be prepared by treating a compound of formula (I) as defined herein, wherein -Alk- is —CH(OR$_2$)-[trans]CH=CH-[cis]CH=CH—CH$_2$-[cis]CH=CH—CH—C$_3$H$_6$—, —(CH$_2$)$_3$—CH(OR$_2$)-[trans]CH=CH-[cis]CH=CH—CH$_2$-[cis]CH=CH—, or —(CH$_2$)$_3$-[cis]CH=CH—CH$_2$-[cis]CH=CH-[trans]CH=CH—CH(OR$_2$)—, and R$_2$ is a hydrogen atom, with a compound of formula Z—(CH$_2$OCH$_2$)$_n$OH are typically commercially available or may be prepared by analogy with known methods.

The present invention also provides a pharmaceutical composition suitable for topical administration comprising a PUFA derivative, as defined herein, or a pharmaceutically acceptable salt, or a solvate thereof, and a pharmaceutically acceptable diluent or carrier, for use in treating skin inflammation, as defined herein, in a mammal, as defined herein.

Preferred pharmaceutical compositions are sterile and pyrogen free.

The pharmaceutical composition is typically in the form of a gel, ointment, cream or lotion.

When said pharmaceutical composition is a gel it typically comprises a hydrophilic polymer such as cross-linked polyethylene glycol, cross-linked starch or polyvinyl pyrrolidone.

An ointment, cream or lotion typically contains an aqueous phase and an oleaginous phase in admixture.

The pharmaceutical composition may additionally contain one or more emollients, emulsifiers, thickeners and/or preservatives, particularly when it is a cream or ointment.

Emollients suitable for inclusion in creams or ointments of the present invention are typically long chain alcohols, for example a C8-C22 alcohol such as cetyl alcohol, stearyl alcohol and cetearyl alcohol, hydrocarbons such as petrolatum and light mineral oil, or acetylated lanolin. The total amount of emollient in the pharmaceutical composition is preferably about 5 wt % to about 30 wt %, and more preferably about 5 wt % to about 10 wt % based on the total weight of the pharmaceutical composition.

The emulsifier is typically a nonionic surface active agent, e.g., polysorbate 60 (available from ICI Americas), sorbitan monostearate, polyglyceryl-4 oleate and poloxyethylene(4) lauryl ether. Generally the total amount of emulsifier is about 2 wt % to about 14 wt %, and more preferably about 2 wt % to about 6 wt % by weight based on the total weight of the pharmaceutical composition.

Pharmaceutically acceptable thickeners, such as Veegum™ K (available from R. T. Vanderbilt Company, Inc.), and long chain alcohols (i.e. C8-C22 alcohols such as cetyl alcohol, stearyl alcohol and cetearyl alcohol) can be used. The total amount of thickener present is preferably about 3 wt % to about 12 wt % based on the total weight of the pharmaceutical composition.

Preservatives such as methylparaben, propylparaben and benzyl alcohol can be present in the pharmaceutical composition. The appropriate amount of such preservative(s) is known to those skilled in the art. The pharmaceutical composition may also comprise a fat-soluble antioxidant such as ascorbyl palmitate, tocopherol and/or ascorbic acid in the presence of lecithin.

Optionally, an additional solubilizing agent such as benzyl alcohol, lactic acid, acetic acid, stearic acid or hydrochloric acid can be included in the pharmaceutical composition. If an additional solubilizing agent is used, the amount present is preferably about 1 wt % to about 12 wt % based on the total weight of the pharmaceutical composition.

Optionally, the pharmaceutical composition can contain a humectant such as glycerin and a skin penetration enhancer such as butyl stearate, urea and DMSO. It is known to those skilled in the art that a single ingredient can perform more than one function in a cream, i.e., cetyl alcohol can serve both as an emollient and as a thickener.

In one embodiment, the pharmaceutical composition is in the form of a cream. The cream typically consists of an oil phase and a water phase mixed together to form an emulsion. Preferably, the cream comprises an oil-in-water emulsion. Preferably, the amount of water present in a cream of the invention is about 45 wt % to about 85 wt % based on the total weight of the cream.

Where the pharmaceutical composition is in the form of an ointment, it is typically comprises a pharmaceutically acceptable ointment base such as petrolatum, or polyethylene glycol 400 (available from Union Carbide) in combination with polyethylene glycol 3350 (available from Union Carbide). The amount of ointment base present in an ointment of the invention is preferably about 660 wt % to about 95 wt % based on the total weight of the ointment.

In the pharmaceutical composition of the present invention, the amount of the PUFA derivative of formula (I) is typically from 0.01 wt % to 50 wt %, preferably from 0.5 wt % to 25 wt %, more preferably from 1 wt % to 10 wt %, for example about 5 wt %, based on the total weight of the pharmaceutical composition.

The compound/composition of the present invention is formulated for topical administration and it may be administered to a patient in an amount such that from 0.00001 to 10 g, preferably from 0.0001 to 1 g active ingredient is delivered per m$^2$ of the area being treated.

Pharmaceutical compositions of the present invention may additionally comprise one or more corticosteroids as defined herein. The amount of the corticosteroid present in the pharmaceutical composition of the invention is typically 50% or less, preferably 25% of less, more preferably 10% or less, most preferably 5% or less, of the recommended amount of said corticosteroid in a commercially available formulation. The skilled person is well aware of the amount of corticosteroids present in various topical formulations. For example, the amount of hydrocortisone present in most commercially available formulations is typically 1% w/w. The amount of clobetasol proprionate present in most commercially available formulations is typically 0.0525% w/w.

Thus, pharmaceutical compositions of the present invention typically comprise hydrocortisone in an amount of 0.5% w/w or less, preferably 0.025% w/w or less, more preferably 0.01% w/w or less, most preferably 0.005% w/w or less. Pharmaceutical compositions of the present invention typically comprise clobetasol proprionate in an amount of 0.026% w/w or less, preferably 0.013% w/w or less, more preferably 0.0053% w/w or less, most preferably 0.0026% w/w or less.

The pharmaceutical compositions of the present invention typically comprise one or more further therapeutic agents, which are not corticosteroids, as defined herein. The amount of the one or more further therapeutic agents, which are not corticosteroids, present in the composition will be evident to the person skilled in the art.

Pharmaceutical compositions of the present invention may be prepared simply by admixing the ingredients in a suitable manner.

The present invention also provides the use of a compound which is a PUFA derivative of formula (I) as defined herein or a pharmaceutically acceptable salt, or solvate thereof, in the manufacture of a medicament for use in treating skin inflammation, as defined herein, in a mammal, as defined herein, by topical administration.

The present invention also provides a method of treating skin inflammation, as defined herein, in a mammal, as defined herein, which method comprises administering to the skin of said mammal a therapeutically effective amount of a compound which is a PUFA derivative of formula (I) as defined herein or a pharmaceutically acceptable salt, or solvate thereof.

The present invention also provides a pharmaceutical composition comprising a polyunsaturated fatty acid (PUFA) derivative of formula (II),

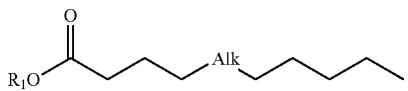

II or a pharmaceutically acceptable salt, or solvate thereof, wherein

-Alk- is —(CH$_2$)$_3$-[cis]CH=CH—CH$_2$-[cis]CH=CH—CH$_2$-[cis]CH=CH—; and

R$_1$ is as defined herein;

which composition is for use in treating skin inflammation in a mammal, by topical administration, and is substantially free of lithium salts and glucocorticoids.

As the skilled person will appreciate, in this embodiment, the pharmaceutically acceptable salt of the PUFA derivative of formula (II) is not a lithium salt.

Typically, the pharmaceutical composition comprising a polyunsaturated fatty acid (PUFA) derivative of formula (II) contains the PUFA derivative of formula (II) as sole active ingredient.

Preferably, the pharmaceutical composition comprising a polyunsaturated fatty acid (PUFA) derivative of formula (II) consists of the PUFA derivative of formula (II) and a pharmaceutically acceptable diluent or carrier, as defined herein.

Preferably, the PUFA derivative of formula (II) is of formula R″(C=O)O—CH$_2$—CH(O(C=O)R″)—CH$_2$—O(C=O)R″, wherein each R″ is the same and is the aliphatic group of dihommo-gamma-linolenic acid, i.e. R″ is —(CH$_2$)$_6$—CH=CH—CH$_2$—CH=CH—CH$_2$—CH=CH—(CH$_2$)$_4$CH$_3$, wherein all of the C=C double bonds have cis configuration. Thus, the PUFA derivative of formula (II) is preferably

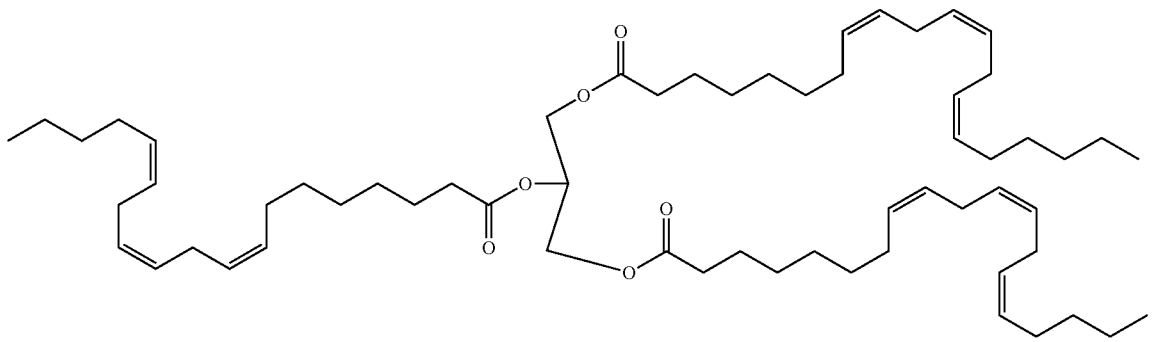 [SMILES: CCCC/C=C\C/C=C\C/C=C\CCCCCCC(=O)OCCC(COC(=O)CCCCCC/C=C\C/C=C\C/C=C\CCCCC)OC(=O)CCCCCC/C=C\C/C=C\C/C=C\CCCC]

In a particularly preferred embodiments, R$_1$ is a hydrogen atom. In this embodiment, the PUFA derivative of formula (II) is DGLA and is represented by the formula

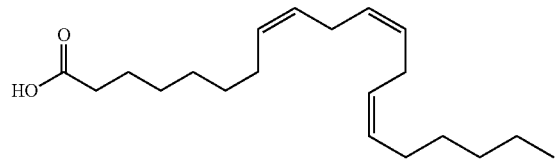 [SMILES: CCCCC/C=C\C/C=C\C/C=C\CCCCCCC(=O)O]

The present invention also provides the use of a pharmaceutical composition comprising a polyunsaturated fatty acid (PUFA) derivative of formula (II) as define herein in the manufacture of a medicament for use in treating skin inflammation, as defined herein, in a mammal, as defined herein, by topical administration, wherein the composition is substantially free of lithium salts and glucocorticoids.

The present invention also provides a method of treating skin inflammation, as defined herein, in a mammal, as defined herein, which method comprises administering to the skin of said mammal a therapeutically effective amount of a pharmaceutical composition comprising a polyunsaturated fatty acid (PUFA) derivative of formula (II) as defined herein, wherein the composition is substantially free of lithium salts and glucocorticoids.

EXAMPLES

Immunohistochemistry analyses were carried out to measure the degree of expression of COX-2 enzymes in ex vivo porcine ear skin. The COX-2 family of enzymes have been strongly linked to inflammation and have been found to be present in increased amounts in inflamed tissue. Thus, a decreased level of COX-2 in the skin corresponds with reduced inflammation of the skin.

Example 1

Freshly excised porcine ears were immersed in iced Hank's buffer for transport from the abattoir to the laboratory. Upon arrival, the porcine ears were first washed with running tap water, and the full thickness skin was liberated from underlying cartilage by blunt dissection using a scalpel and hairs were removed with an electrical razor. The skin was used within 2 h of slaughter. The full thickness skin was cut into approximately 2 cm×2 cm and placed in Hanks balance salt to maintain skin viability.

A 2 mm strip of skin was obtained using a surgical scalpel and the skin strip then fixed using a 40% formaldehyde solution, dehydrated and set in molten wax. The sections were cut using a Shandon Finesse microtome (Thermo Scientific, Waltham, Mass., USA) to a thickness of 5 µm and were placed onto 2.5 cm×7.5 cm×1 mm pre-cleaned microslides. The section of skin was stained with diaminobenzidine, which binds to COX-2 enzymes and the slides visualised on a light microscope with image capture facility.

Skin membranes were mounted in Franz diffusion cells using Hanks buffer as receptor phase. Water was used as the donor phase. After 6 hours the skin was removed from the Franz cell apparatus, excess donor phase was removed and the skin wiped clean with a clean paper tissue. The diffusional area was then cut into approximately 2 mm strips using a surgical scalpel and the skin strips then using a 40% formaldehyde solution, dehydrated and set in molten mass. The sections were cut using a Shandon Finesse microtome (Thermo Scientific, Waltham, Mass., USA) to a thickness of 5 µm and were placed onto 2.5 cm×7.5 cm×1 mm pre-cleaned microslides. The section of skin was stained with diaminobenzidine, which binds to COX-2 enzymes, and the slides visualised on a light microscope with image capture facility.

The results of this experiment are shown as FIG. 1. A dark stain is present in the sample both after 0 hours and 6 hours, indicating the continuing presence of COX-2 in the skin. This indicates that water has no anti-inflammatory activity.

Example 2

An experiment was carried out as described in Example 1, except that the donor phase comprised ketoprofen, a known COX-2 inhibitor, in fish oil.

Figure 2:
FIG. 2 shows the results of an immunohistochemistry assay to determine the amount of COX-2 enzymes present in ex vivo porcine ear skin, which has been treated with ketoprofen in fish oil, 0 and 6 hours after staining with diaminobenzidine.
Figure 2:

The results of this experiment are shown in FIG. 2. After six hours, the amount of dark stain has reduced, indicating penetration of ketoprofen into the viable epidermis and activity against COX-2 expression in the skin.

Example 3

An experiment was carried out as described in Example 1, except that the donor phase comprised a representative compound of the invention, DGLA.

Figure 3:
FIG. 3 shows the results of an immunohistochemistry assay to determine the amount of COX-2 enzymes present in ex vivo porcine ear skin, which has been treated with a representative compound of the invention, DGLA, 0 and 6 hours after staining with diaminobenzidine.
Figure 3:
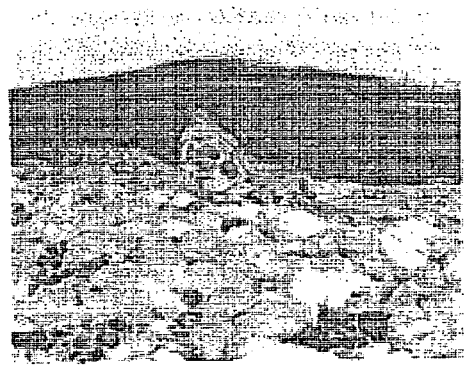

The results of this experiment are shown in FIG. 3. After six hours, the amount of dark stain has reduced, indicating penetration of DGLA into the viable epidermis and activity against COX-2 expression in the skin.

Example 4

An experiment was carried out as described in Example 1, except that the donor phase comprised a representative compound of the invention, 15-HETrE.

Figure 4:
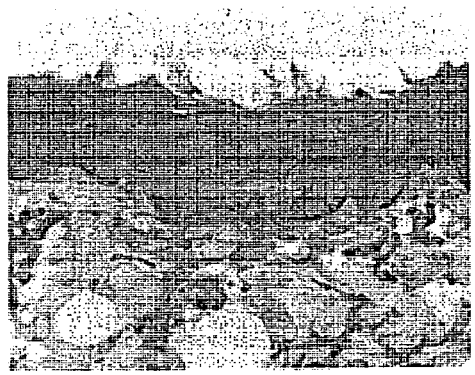
FIG. 4 shows the results of an immunohistochemistry assay to determine the amount of COX-2 enzymes present in ex vivo porcine ear skin, which has been treated with a representative compound of the invention, 15-HETrE, 0 and 6 hours after staining with diaminobenzidine.
Figure 4:
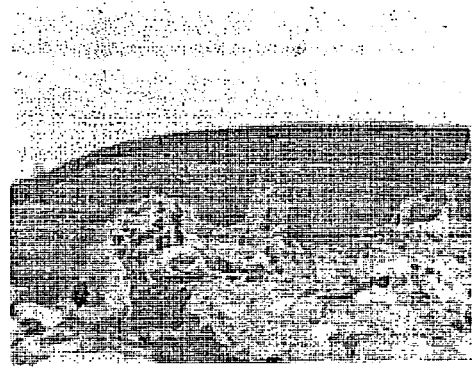

The results of this experiment are shown as FIG. 4. After six hours, the amount of dark stain has reduced, indicating penetration of 15-HETrE into the viable epidermis and activity against COX-2 expression in the skin.

Example 5

A Western Blotting experiment was carried out to determine the effective of topically applied representative compounds of the invention DGLA and 15-HETrE on the expression of COX-2 in porcine skin. Water was used as a control.

The porcine skin membranes (as described in Example 1) were gently cleaned with de-ionised water before being homogenized (Silverson, Chesham, UK) in a RIPA lysis buffer [50 mM Tris-HCl (pH 7.4), 150 mM NaCl, 1 mM PMSF, 1 mM EDTA, 5 µmL$^{-1}$ aprotinin, 5 µg mL$^{-1}$ leupeptin, 1% Triton X-100, 1% sodium deoxycholate, 0.1% SDS]. After 15 min incubation on ice, the lysates were clarified by centrifugation at 14000×g for 2×15 min and the supernatant stored at −80° C. for subsequent protein analysis.

Aliquots of 30 µg total protein were separated by SDS-PAGE, transferred to nitrocellulose membranes using the Trans-Blot electrophoretic Transfer Cell and briefly stained with Ponceau S to verify effective transfer. Immunoblots were incubated for 1 h in a blocking solution [tris-buffered saline (TBS)-Tween 20 containing 5% (w/v) commercial skimmed milk powder (Marvel) at room temperature. After washing, the membrane was probed overnight at 4° C. with COX-2 antibody at 1:1000, 5-LOX at 1:1000 and iNOS at 1:500 in (1:20 and 1:100 western blocking reagent and sodium azide solution respectively made up to volume with TBS tween). Membranes were then incubated for 1 h with HRP-conjugated anti-rabbit at 1:10000. For β-actin, membranes were probed with anti-actin and anti-mouse for 1 h each at room temperature at 1:10000. After 3×10 min washes in TBS Tween, they were finally exposed to freshly prepared Dura Substrate for chemiluminescence for appropriate time before performing autoradiography.

Figure 5:
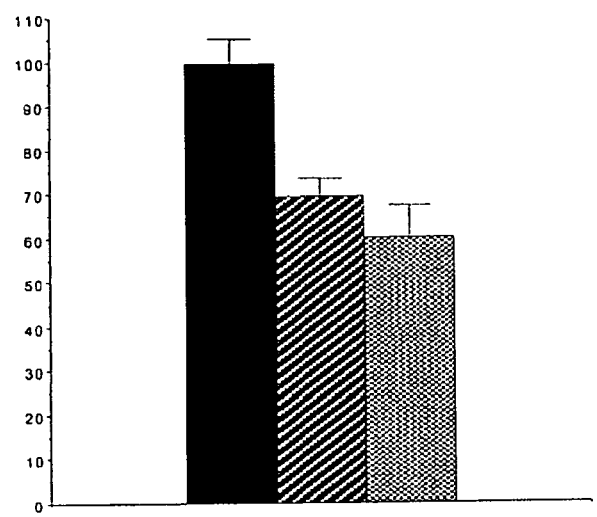
FIG. 5 shows the results of a Western Blotting analysis to determine the effect of DGLA (second bar) and 15-HETrE (third bar) on COX-2 expression in porcine skin relative to water (first) bar. Levels in control were assigned a value of 100%.

The results of this experiment are shown as FIG. 5. It can be seen that a significant reduction in COX-2 expression is seen following dosing with DGLA and 15-HETrE, relative to the control.

What is claimed is:

1. A method of treating uremic pruritus in a subject in need thereof, the method comprising administering a therapeutically effective amount of a composition comprising DGLA or-15-HETrE, or an ester or pharmaceutically acceptable salt thereof, to skin of the subject.

2. The method of claim 1, wherein the composition comprises about 0.01 wt % to about 50 wt % 15-HETrE.

3. The method of claim 1, wherein the composition comprises about 0.01 wt % to about 50 wt % DGLA.

4. The method of claim 1, wherein the composition comprises about 0.01 wt % to about 25 wt % 15-HETrE.

5. The method of claim 1, wherein the composition comprises about 0.01 wt % to about 25 wt % DGLA.

6. The method of claim 1, wherein the composition comprises about 1 mg to about 1000 mg of DGLA.

7. The method of claim 1, wherein the composition comprises about 1 mg to about 1000 mg of 15-HETrE.

8. The method of claim 1, wherein the composition is administered topically to the skin of the mammal.

9. The method of claim 1, wherein the composition further comprises a pharmaceutically acceptable diluent or carrier.

10. The method of claim 1, wherein the composition comprises about 1 mg to about 1,000 mg of 15-HETrE.

11. The method of claim 8, wherein the composition is administered in an amount sufficient to deliver 0.00001 g to 10 g of 15-HETrE per square meter of skin.

12. The method of claim 8, wherein the composition is administered in an amount sufficient to deliver 0.0001 g to 1 g of 15-HETrE per square meter of skin.

13. The method of claim 1, wherein the composition is co-administered with a corticosteroid selected from the group consisting of clobetasol diproprionate, betamethasone diproprionate, halbetasol proprionate, diflorasone diacetate, fluocinonide, halcinonide, amcinonide, desoximetasone, triamcinolone acetonide, mometasone furoate, fluticasone proprionate, fluocinolone acetonide, hydrocortisone valerate, hydrocortisone butyrate, triamcinalone acetonide, desonide, prednicarbate, prednisolone, methylprednisolone, dexamethasone, naflocort, deflazacort, halopredone acetate, budesonide, beclomethasone dipropionate, hydrocortisone, clocortolone pivalate, methylprednisolone aceponate, dexamethasone palmitoate, tipredane, hydrocortisone aceponate, alclometasone dipropionate, halometasone, methylprednisolone suleptanate, rimexolone, prednisolone farnesylate, ciclesonide, deprodone propionateloteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate, hydrocortisone probutate, and combinations thereof.

14. The method of claim 13, wherein the corticosteroid is co-administered in an amount sufficient to provide 50% or less of the recommended daily dosage of said corticosteroid in said mammal.

15. The method of claim 14, wherein the corticosteroid is hydrocortisone.

16. The method of claim 1, wherein the composition is co-administered with a further therapeutic agent selected from the group consisting of immunomodulators, antibiotics, immunosuppressants, and anti-itch drugs.

17. A method of treating itching of the skin in a mammal, the method comprising administering to the mammal a composition comprising a therapeutically effective amount of a compound of Formula (I):

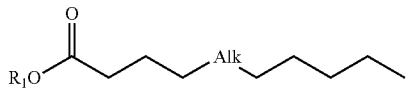

Formula (I)

or a pharmaceutically acceptable salt thereof, wherein
-Alk- is —(CH$_2$)$_3$-[cis]CH=CH—CH$_2$-[cis]CH=CH-[trans]CH=CH—CH(OR$_2$)—;
R$_1$ is selected from the group consisting of: hydrogen; C$_1$-C$_6$ alkyl; C$_2$-C$_6$ alkenyl; C$_2$-C$_6$ alkynyl; C$_6$-C$_{10}$ aryl; 5- to 10-membered heteroaryl; C$_3$-C$_7$ carbocyclyl or 5- to 10-membered heterocyclyl group; a group of formula —CH$_2$—CH(OR$_3$)—CH$_2$-(OR$_4$) wherein R$_3$ and R$_4$ are each independently hydrogen atoms or —(C=O)—R$_6$, wherein R$_6$ is an aliphatic group having from 3 to 29 carbon atoms; and a group of formula —(CH$_2$OCH$_2$)$_m$OH, wherein m is an integer from 1 to 200;
R$_2$ is selected from the group consisting of:
a hydrogen atom;
a group of formula —(C=O)—R$_5$, wherein R$_5$ is a C$_1$-C$_6$ alkyl, C$_2$-C$_6$ alkenyl, C$_2$-C$_6$ alkynyl, C$_6$-C$_{10}$ aryl, 5- to 10-membered heteroaryl, C$_3$-C$_7$ carbocyclyl or 5- to 10-membered heterocyclyl group;
an aliphatic group having from 3 to 29 carbon atoms; and
a group of formula —(CH$_2$OCH$_2$)—OH, wherein n is an integer of from 1 to 200; and
wherein said alkyl, alkenyl, alkynyl and aliphatic groups are the same or different and are each unsubstituted or substituted with 1, 2 or 3 unsubstituted substituents which are the same or different and are selected from halogen atoms and C$_1$-C$_4$ alkoxy, C$_2$-C$_4$ alkenyloxy, C$_1$-C$_4$ haloalkyl, C$_2$-C$_4$ haloalkenyl, C$_1$-C$_4$ haloalkoxy, C$_2$-C$_4$ haloalkenyloxy, hydroxyl, —SR', and —NR'R" groups where R' and R" are the same or different and represent hydrogen or unsubstituted C$_1$-C$_2$ alkyl; said aryl, heteroaryl, carbocyclyl and heterocyclyl groups are the same or different and are each unsubstituted or substituted by 1, 2, 3 or 4 unsubstituted substituents which are the same or different and are selected from halogen atoms, and cyano, nitro, C$_1$-C$_4$ alkyl, C$_1$-C$_4$ alkoxy, C$_2$-C$_4$ alkenyl, C$_2$-C$_4$ alkenyloxy, C$_1$-C$_4$ haloalkyl, C$_2$-C$_4$ haloalkenyl, C$_1$-C$_4$ haloalkoxy, C$_2$-C$_4$ haloalkenyloxy, hydroxyl, C$_1$-C$_4$ hydroxyalkyl, —SR' and —NR'R" groups wherein each R' and R" is the same or different and represents hydrogen or unsubstituted C$_1$-C$_4$ alkyl.

18. The method of claim 17, wherein:
R$_1$ is hydrogen or C$_1$-C$_6$ alkyl; and
R$_2$ is a hydrogen atom or an aliphatic group having from 3 to 29 carbon atoms.

19. A method of treating itching of the skin in a mammal, the method comprising administering to the mammal a composition comprising a therapeutically effective amount of a compound of formula:

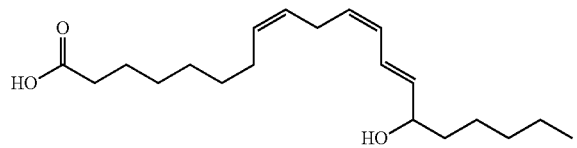 [SMILES: CCCCCC(O)/C=C/C=C\C/C=C\CCCCCCC(=O)O]

or a pharmaceutically acceptable salt thereof.

* * * * *